United States Patent [19]

Finsterwald et al.

[11] 4,426,886

[45] Jan. 24, 1984

[54] ULTRASONIC SCANNER

[75] Inventors: P. Michael Finsterwald; LeRoy Kopel, both of Tempe, Ariz.

[73] Assignee: Advanced Diagnostic Research Corporation, Tempe, Ariz.

[21] Appl. No.: 319,448

[22] Filed: Nov. 9, 1981

[51] Int. Cl.³ .............................................. G01N 29/04
[52] U.S. Cl. ....................................................... 73/633
[58] Field of Search ........................... 73/633, 621, 620; 128/660

[56] References Cited

U.S. PATENT DOCUMENTS

| 2,602,102 | 7/1952 | Webb | 73/633 X |
| 3,996,792 | 12/1976 | Kubota et al. | 73/62 X |
| 4,092,867 | 6/1978 | Matzuk | 73/621 X |
| 4,130,021 | 12/1978 | Mueller et al. | 73/633 |
| 4,181,120 | 1/1980 | Kunii et al. | 73/620 X |

Primary Examiner—Anthony V. Ciarlante
Attorney, Agent, or Firm—Lawrence S. Levinson; Sanford J. Asman

[57] ABSTRACT

In a mechanical sector scanner, a first bevel gear is mounted on the end of an output shaft of a motor, and an ultrasonic transducer is rotatably supported for rotating about a scanning axis transverse to the output shaft. A second bevel gear engaging the first bevel gear is mounted on the back surface of the transducer. The output shaft oscillates about an output axis. Oscillations of the output shaft are coupled to the transducer by the bevel gears. The second gear has a plurality of teeth arranged in an arc less than completely around the scanning axis, and the second gear is so disposed that the back surface of the transducer is nearer to the scanning axis than the teeth.

24 Claims, 5 Drawing Figures

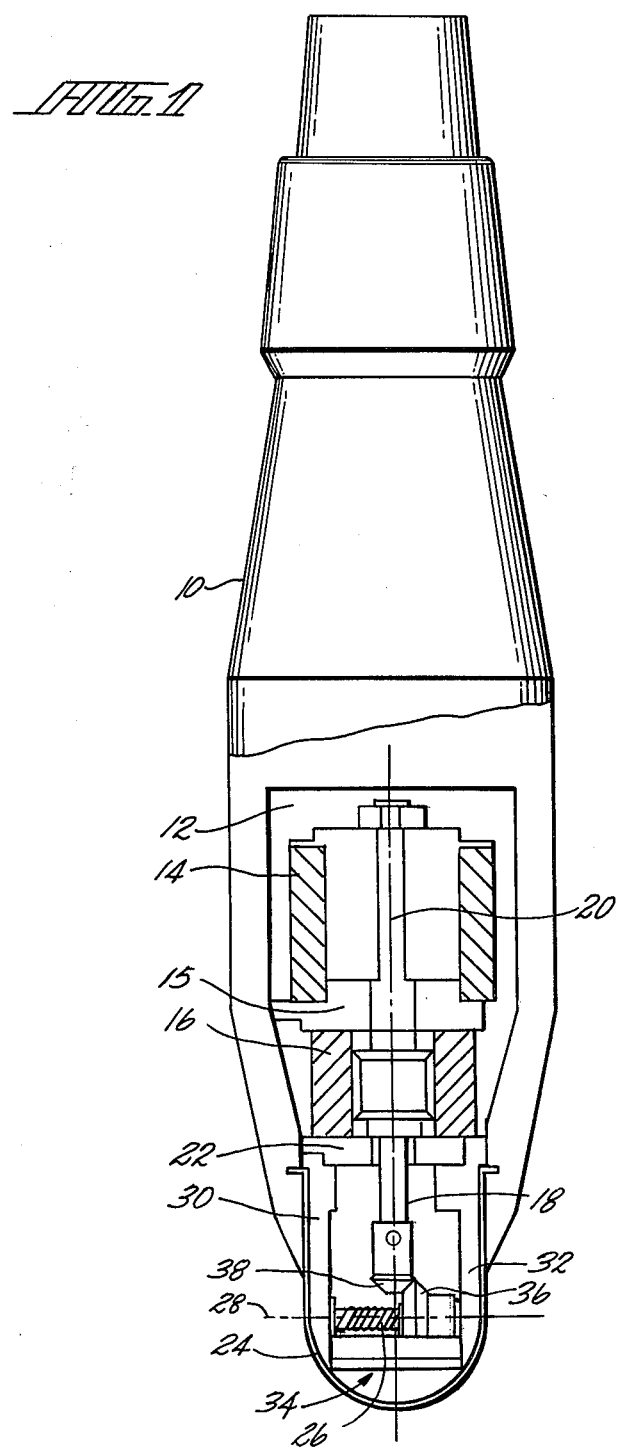

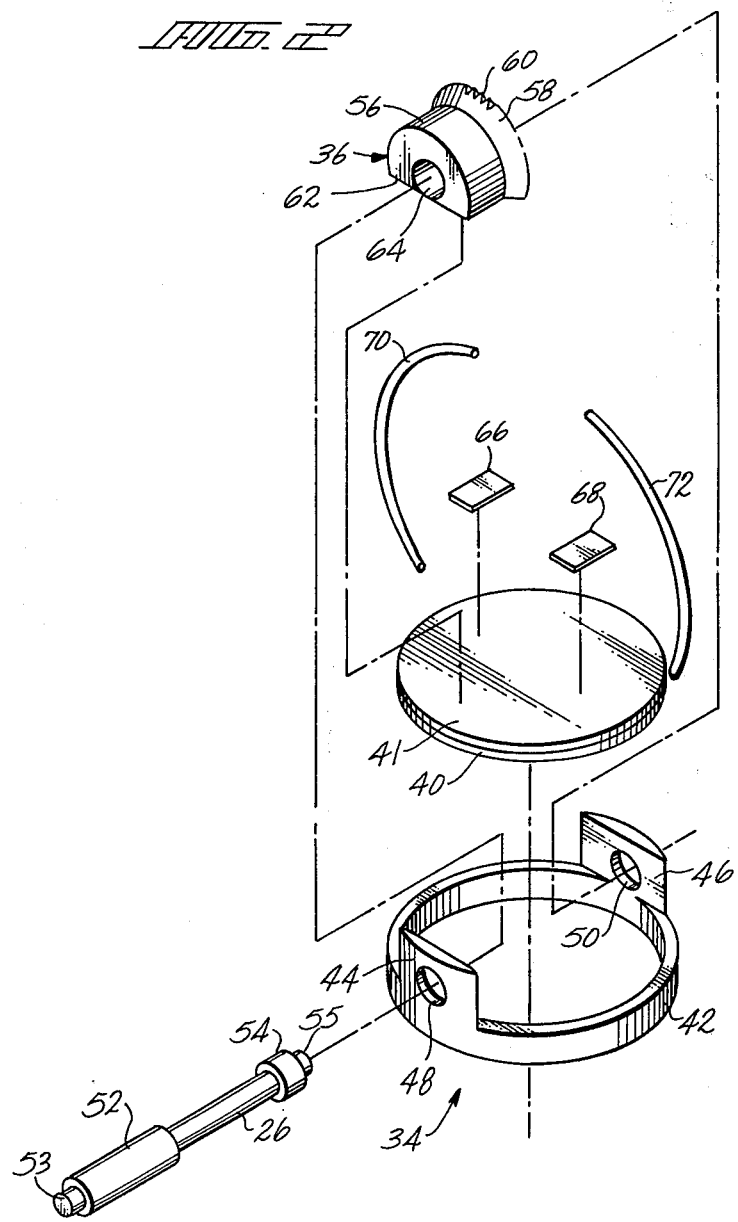

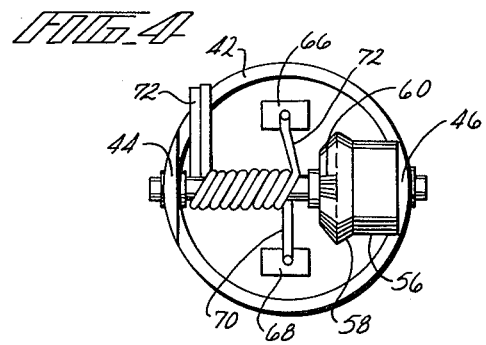
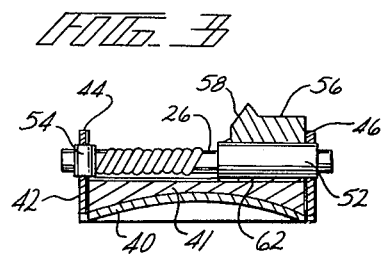
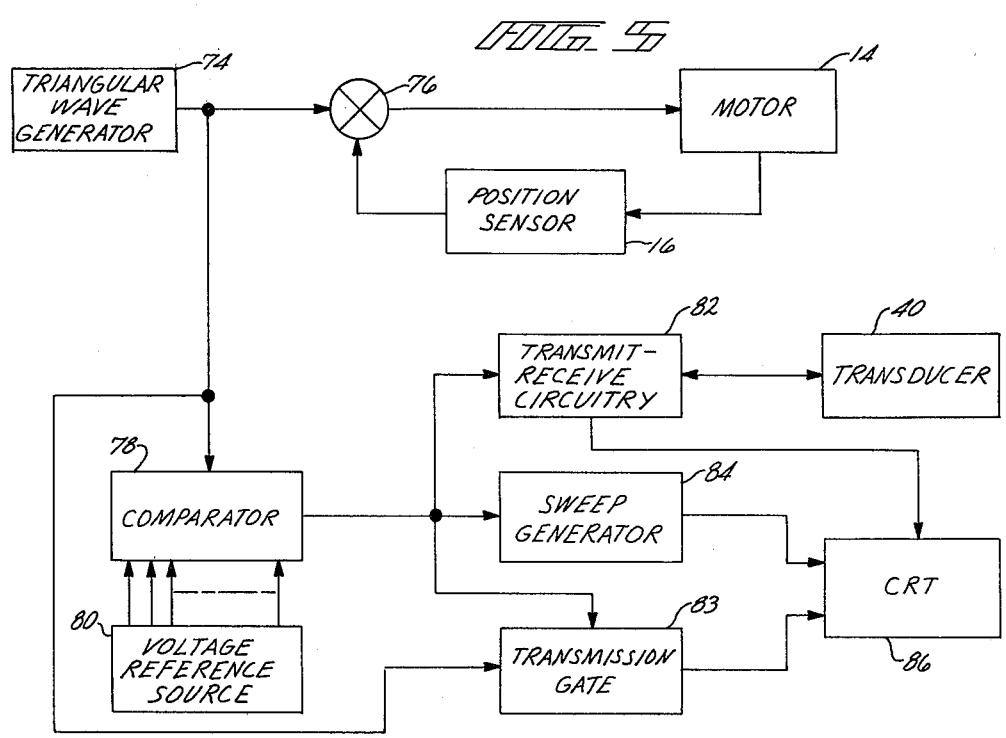

ULTRASONIC SCANNER

BACKGROUND OF THE INVENTION

This invention relates to ultrasonic interrogation and, more particularly, to a mechanical ultrasonic scanner of the type typically used in medical diagnosis.

Mechanical ultrasonic sector scanners are commonly used in medical diagnosis. Such a scanner has in a hand held housing an ultrasonic transducer that rotates or oscillates to transmit ultrasonic energy to a sectorial area and receive echos therefrom. A signal representative of the received echoes modulates the beam of a cathode ray tube. The beam is controlled to represent on the screen the sector being scanned. As a result, the cathode ray tube displays an image of the scanned sector, which can be used for medical diagnosis when parts of the human body are interrogated by the scanner.

Numerous arrangements have been devised to drive an ultrasonic transducer mechanically so as to effect a sector scan. For example, Matzuk U.S. Pat. No. 4,092,867 discloses an ultrasonic transducer secured to a permanent magnet. The transducer and magnet are mounted for rotation between a pair of magnetic armature poles around which a pair of servo drive coils are wound. The coils are connected to the output of a servo amplifier to which a signal representative of the angular position of the ultrasonic transducer and a signal representative of the desired angular position are applied.

Connell et al U.S. Pat. No. 4,149,419 discloses a rotor on which four ultrasonic transducers are mounted at 90 degree intervals. The rotor is continuously driven by a motor about an axis perpendicular to the axis of rotation of the motor shaft and the transducers are individually activated as they pass through a given sector of each rotor revolution.

Paton et al U.S. Pat. No. 4,120,291 discloses an ultrasonic probe, pivotally attached at one end to the periphery of a continuously rotating crank. The other end of the probe at which an ultrasonically active surface is disposed is secured to a scanner housing by a rolling diaphragm. The probe is constrained by a pair of plates to move in a single plane so as to oscillate back and forth in the plane as the crank rotates.

The number of frames per second of visually displayed data that can be collected by a mechanical sector scanner depends upon the motor load including the moment of inertia of the rotating or oscillating transducer assembly connected to the motor. If the load becomes too great, perceptible vibration occurs, which degrades the image displayed by the CRT. Thus an important characteristic of a mechanical sector scanner is a small moment of inertia. Another desirable characteristic is compactness of component layout within the housing.

SUMMARY OF THE INVENTION

According to the invention, the output shaft of a motor that oscillates about an output axis. is coupled to an ultrasonic transducer by a right-angle drive. A first bevel gear having gear teeth is mounted on the end of the output shaft. The transducer has a front-radiating surface and a back mounting surface on which a second bevel gear is mounted. The second gear has gear teeth distributed in an arc less than completely around an axis of rotation such that the back surface of the transducer is spaced nearer to the axis of rotation than those teeth of the second gear located diametrically opposite the back surface. The transducer and the second gear are rotatably supported for rotation about the axis of rotation with the gear teeth of the first and second gears in engagement and the axis transverse to the output shaft. Oscillations of the output shaft are coupled to the transducer by the bevel gears. As a result of the described bevel gear coupling, the transducer and its mounting structure possess a smaller moment of inertia in a compact arrangement, thereby presenting to the output shaft of the motor a smaller load. Consequently, a motor having a given output torque can drive the ultrasonic transducer at a higher angular velocity, thereby increasing the lines and/or frames displayed on a CRT screen.

A feature of the invention is the use of flexible leads for the transducer that are wrapped around the transducer scanning shaft so as to unwind during one direction of rotation and to wind during the opposite direction of rotation.

BRIEF DESCRIPTION OF THE DRAWINGS

The features of a specific embodiment of the best mode contemplated of carrying out the invention are illustrated in the drawings in which:

FIG. 1 is a side-sectional view of the hand held portion of a mechanical ultrasonic sector scanner incorporating principles of the invention;

FIG. 2 is an exploded view of the ultrasonic transducer assembly of the scanner of FIG. 1;

FIG. 3 is a side-sectional view of the ultrasonic transducer assembly of the scanner of FIG. 1;

FIG. 4 is a top plan view of the ultrasonic transducer assembly of the scanner of FIG. 1; and FIG. 5 is a schematic block diagram of the electronics of the scanner of FIG. 1.

DETAILED DESCRIPTION OF THE SPECIFIC EMBODIMENT

In FIG. 1 the hand-held portion of a mechanical ultrasonic sector scanner comprises a housing 10 in which a sealed chamber 12 is formed. A motor 14 and an angular position sensor 16 are disposed in chamber 12. Motor 14 is mounted on housing 10 by a bracket 15. Motor 14 has an output shaft 18 that oscillates about an output axis 20 through an angle smaller than 180°. Typically the range of oscillations would be of the order of 90° and the corresponding section scan would possess an included angle of 90°. Axis 20 is aligned with the longitudinal axis of housing 10. By way of example, motor 14 could comprise a limited angle torque motor such as, for example, a wide angle limited rotation brushless D.C. torque motor, Model TQ 10Y-4 of Aeroflex Laboratories Inc. Plainview, N.Y. Position sensor 16 has a stationary part mounted on housing 10 by a bracket 22, and a movable part mounted on shaft 18. By way of example, position sensor 16 could comprise a differential transformer RVDT such as Model 20602, Pickering & Co., Inc., Plainview, N.Y. Housing 10 is open at one end. Output shaft 18 extends through chamber 12 to a point near the open end of housing 10, where a cap 24 transparent to ultrasonic energy covers and seals the open end of housing 10. A scanning shaft 26 is spaced from the end of output shaft 18. Shaft 26 has a scanning axis 28 that is transverse, preferably perpendicular, to output axis 20. The ends of shaft 26 are supported within housing 10 by brackets 30 and 32, respectively. The ends of shaft 26 are journaled for rotation by ball bearings (not shown) pressed into bores formed in brackets 30 and 32, respectively. An ultrasonic transducer assembly 34 including a bevel gear 36 is mounted for rotation on shaft 26. A bevel gear 38, which engages bevel gear 36 is fixedly secured to the end of output shaft 18. Thus, the oscillations of output shaft 18 caused by the energization of motor 14 are transformed by bevel gears 36 and 38, functioning as a right-angle drive, into oscillations of transducer assembly 34 about an axis transverse to the axis of motor 14. Chamber 12 is filled with a fluid, such as water, having approximately the same speed of sound as the medium, e.g., body tissue, being interrogated by the ultrasonic energy from the scanner. The end of cap 24 is spherical. Thus, the distance that the ultrasonic energy travels through the fluid between transducer assembly 34 and cap 24 is the same for all angular positions of transducer assembly 34 within the sector scan.

With reference to FIGS. 2, 3 and 4, transducer assembly 34 comprises a disc-shaped preferably focussed piezoelectric element 40 with a concave or flat front surface and a body 41 of sound damping material on the back surface of element 40. Body 41 has a flat surface that abuts bevel gear 36 as shown in FIG. 3. Transducer assembly 34 could be constructed by several well-known techniques, including the manner disclosed in U.S. Pat. No. 4,148,094, which issued Jan. 15, 1980. The disclosure of this patent is incorporated fully herein by reference. Element 40 fits into a support ring 42 where it is bonded in place and then the sound damping material is poured into the space within ring 42 in molten form. When the sound damping material hardens, it forms body 41. Ring 42 has oppositely disposed collet forming extensions 44 and 46 in which bores 48 and 50, respectively, are formed. The outer surfaces of extensions 44 and 46 are curved to conform to the outer surface of ring 42 and the inner surfaces of extensions 44 and 46 are flat. As clearly illustrated in FIG. 2, gear 36 has a generally cylindrical body 56 and a crown 58 on which gear teeth 60 are formed. Gear teeth 60 mesh with corresponding gear teeth on gear 38. Part of gear 36 is cut away leaving on the side thereof opposite teeth 60 a flat mounting face 62. An axial bore 64 is formed through gear 36 near face 62. Bores 48 and 64 receive an enlarged diameter portion 52 of shaft 26. Bore 50 receives an enlarged diameter portion 54 on shaft 26. Shaft 26 is bonded to ring 42 and gear 36 to become part of transducer assembly 34. Ends 53 and 55 of shaft 26 outboard of portions 52 and 54 are journaled for rotation in brackets 30 and 32 as described above. Face 62 abuts the flat back surface of body 41. If desired, gear 36 could be secured to body 41 by bonding. Gear 36, element 40, body 41, ring 42, and shaft 26 rotate with respect to housing 10. Gear 36 is arranged within the perimeter of ring 42, thereby providing a compact component layout. By virtue of flat face 62, the back surface of body 41 is nearer to scanning axis 28 than teeth 60 and the periphery of cylindrical portion 56 and crown portion 58 opposite flat face 62. This asymmetrical coupling arrangement provides a small moment arm for transducer assembly 34 and thus a small moment of inertia. Consequently, assembly 34 can be rotated at faster angular speed, thereby permitting a larger frame rate on a CRT screen without perceptible vibration. In a typical example, 25 or 30 frames per second can be displayed without image degradation due to vibration. This large frame rate permits motion of the interrogated object to be effectively captured and displayed.

Electrically conductive terminal pads 66 and 68 are formed on the back surface of body 41. As depicted in FIG. 4, terminal pads 66 and 68 are disposed adjacent to opposite sides of shaft 26 near bevel gear 36. Insulated flexible leads 70 and 72 are wrapped around shaft 26 in the same direction. By way of example, leads 70 and 72 could be Flexileads sold by Cooner Wire of Chatsworth, California. One end of lead 70 is electrically connected to pad 66, for example, by soldering. One end of lead 72 is electrically connected to pad 68, for example, by soldering. Sufficient slack is left in the ends of leads 70 and 72 connected to pads 66 and 68 to accommodate the oscillation of element 40. Thus, as element 40 oscillates in one direction, the ends of leads 70 and 72 wind around shaft 26 and as element 40 oscillates in the other direction, the ends of leads 70 and 72 unwind from shaft 26. The other ends of leads 70 and 72 are connected to the transmit-receive circuitry described below in connection with FIG. 5. Wrapping leads 70 and 72 around shaft 26 provides stress relief for leads 70 and 72 and a convenient and controlled routing path between the transmit-receive circuitry and element 40.

In FIG. 5 the output of a triangular wave generator 74 is coupled to the input of a summing junction 76, to the input of a comparator 78, and to the transmitting input of a transmission gate 83. The output of position sensor 16 is coupled to the other input of summing junction 76. The output of summing junction 76 is coupled to the control input of motor 14. Wave generator 74 produces a periodic voltage that varies linearly from a low value to a high value and then returns linearly to the low value. Position sensor 16 produces a voltage proportional to the angular position of the output shaft of motor 14. Motor 14 is driven responsive to the difference between the voltages produced by wave generator 74 and position sensor 16, so the latter tends to track the former, thereby causing the angular position of first angular position to a second angular position and then linearly return from the second angular position to the first angular position. The linear oscillation of the output shaft of motor 14 produce a linear sector scan of element 40. A voltage reference source 80 has a number of outputs equal to the number of lines in the display. These outputs are applied to comparator 78 for comparison with the voltage from wave generator 74. The voltage value of each output from reference source 80 corresponds to a different line of display. Each time the voltage produced by wave generator 74 coincides with one of the voltage values from reference source 80, comparator 78 produces a trigger pulse at its output, which is coupled to the trigger input of transmit-receive circuitry 82, the trigger input of a sweep generator 84, and the gating input of transmission gate 83. Responsive to each trigger pulse, transmit-receive circuitry 82 energizes element 40 in well known fashion to emit a burst of ultrasonic energy, sweep generator 84 initiates a sweep voltage corresponding to distance from the transducer in the direction of emitted energy, and transmission gate 83 passes the voltage from wave generator 74, which corresponds to the angular position of element 40. Echoes of the emitted burst of ultrasonic energy, returned to element 40 are coupled to the beam modulating input of a cathode ray tube (CRT) 86. The sweep voltage from sweep generator 84 and the voltage from wave generator 74 are applied to the respective beam deflection inputs of CRT 86 to produce a B-scan sector display on its screen.

The described embodiment of the invention is only considered to be preferred and illustrative of the inventive concept; the scope of the invention is not to be restricted to such embodiment. Various and numerous other arrangements may be devised by one skilled in the art without departing from the spirit and scope of this invention. For example, other right-angle drive arrangements might be employed, although that disclosed has resulted in the lowest moment of inertia. Or the invention could be used to produce an A-scan display of an object within the scanned sector.

What is claimed is:

1. A mechanical ultrasonic scanner comprising:
   a motor having an output shaft that oscillates about an output axis;
   a first bevel gear having teeth mounted on the end of the output shaft;
   an ultrasonic transducer spaced from the end of the output shaft, the transducer having a front radiating surface and a back mounting surface;
   a second bevel gear mounted on the back surface of the transducer, the second gear having gear teeth distributed in an arc less than completely around an axis of rotation such that the back surface of the transducer is spaced nearer to the axis of rotation than those teeth of the second gear located diametrically opposite the back surface; and
   means for rotatably supporting the transducer and the second gear for rotation about the axis of rotation with the gear teeth of the first and second gears in engagement and the axis of rotation transverse to the output axis.

2. The scanner of claim 1, in which the supporting means comprises a rotatable scanning shaft on which the second gear and the transducer are fixedly mounted for rotation as a unit with the scanning shaft.

3. The transducer of claim 2, additionally comprising a transit-receive circuit, a pair of electrical terminals on the transducer, and a pair of flexible leads between the circuit and the respective terminals, the leads being wrapped around the scanning shaft in the same direction with sufficient slack to accommodate oscillation of the transducer.

4. The scanner of claim 2 in which the back surface is flat and the second bevel gear has a flat face abutting the back surface of the second gear.

5. The scanner of claim 4, in which the edge surface of the transducer is circular and the transducer supporting means additionally comprises a ring into which the transducer fits, the ring having spaced apart collets that receive the scanning shaft for rotation therein.

6. The transducer of claim 5, in which the second gear has a bore near the flat face thereof that receives the scanning shaft.

7. The transducer of claim 6, additionally comprising a transit-receive circuit, a pair of electrical terminals on the transducer, and a pair of flexible leads between the circuit and the respective terminals, the leads being wrapped around the scanning shaft in the same direction with sufficient slack to accommodate oscillation of the transducer.

8. The scanner of claim 6, in which the outer surfaces of the collets are curved to conform to the outer surface of the ring.

9. The scanner of claim 1, in which the transducer has a thin shape with a front focussed ultrasonic radiating surface, the back mounting surface is flat, and an edge surface is formed between the mounting surface and the radiating surface.

10. The scanner of claim 9, in which the second gear has opposite the teeth a flat face that abuts the flat mounting surface.

11. The transducer of claim 10, in which the second gear has a bore near the flat face thereof that receives the scanning shaft.

12. The scanner of claim 1, in which the output shaft of the motor oscillates through an angle smaller than 180°.

13. The scanner of claim 1, additionally comprising a housing in which the motor is mounted, the housing having an open end to which the output shaft extends such that the bevel gears and the transducer are located outside the housing, and a cap transparent to ultrasonic energy covering the open end of the housing including the first and second bevel gears and the transducer.

14. The scanner of claim 13, in which the supporting means comprises a rotatable scanning shaft in the cap on which the second gear and the transducer are fixedly mounted for rotation as a unit with the scanning shaft.

15. The scanner of claim 14, in which the supporting means additionally comprises a pair of stationary, spaced apart brackets within the cap and means for journalling the scanning shaft for rotation relative to the pair of brackets.

16. The scanner of claim 15, in which the end of the cap is spherical and has a center located to coincide with the intersection of the axis of rotation and the axis of the output shaft.

17. The scanner of claim 16, in which the cap is filled with a fluid.

18. The scanner of claim 17, in which the fluid has approximately the same speed of sound as body tissue.

19. A mechanical ultrasonic scanner comprising:
   a motor having an output shaft that oscillates about an output axis;
   a transducer spaced from the end of the output shaft;
   a scanning shaft for rotatably supporting the transducer to rotate about a scanning axis transverse to the output axis;
   means for coupling oscillations of the output shaft to the scanning shaft;
   a transmit-receive circuit;
   a pair of electrical terminals on the transducer; and
   a pair of flexible leads between the circuit and the respective terminals, the leads being wrapped around the scanning shaft with sufficient slack to accommodate oscillation of the transducer such that the leads unwind during one direction of rotation of the scanning shaft and wind during the other direction of rotation of the scanning shaft.

20. The scanner of claim 19, in which the scanning shaft is rotatable and the transducer is fixed thereon for rotation therewith.

21. A mechanical ultrasonic scanner comprising:
   a motor having an output shaft that oscillates about an output axis;
   an ultrasonic transducer spaced from the end of the output shaft;
   means for rotatably supporting the transducer for rotation about a scanning axis perpendicular to the output axis;
   a first bevel gear having teeth mounted on the end of the output shaft;
   a second bevel gear mounted on the back of the transducer, the second gear having gear teeth distributed in an arc less than completely around an axis of rotation such that the back surface of the transducer is spaced nearer to the axis of rotation than those teeth of the second gear located diametrically opposite the back surface;

means for periodically energizing the transducer to emit periodic ultrasonic energy pulses as the transducer oscillates; and means for visually displaying the echoes received by the transducer as it oscillates.

22. The scanner of claim 21, additionally comprising a triangular wave generator, means for sensing the angular position of the transducer, and means for controlling the motor responsive to the triangular wave generator and the position sensing means so the output shaft of the motor tracks the triangular generator.

23. The scanner of claim 22, additionally comprising a housing having a longitudinal axis, the motor and the sensing means being located in the housing such that the output shaft is aligned with the longitudinal axis of the housing.

24. The scanner of claim 23, in which the sensing means has a first part mounted on the output shaft between the motor and the first gear and a second part mounted on the housing adjacent to the first part.

* * * * *